United States Patent

Karg et al.

[11] 4,220,777
[45] Sep. 2, 1980

[54] NAPHTHALIMIDE DERIVATIVES

[75] Inventors: Jochen Karg, Ludwigshafen; Manfred Patsch; Walter Himmele, both of Wachenheim, all of Fed. Rep. of Germany

[73] Assignee: BASF Aktiengesellschaft, Ludwigshafen, Fed. Rep. of Germany

[21] Appl. No.: 961,485

[22] Filed: Nov. 17, 1978

[30] Foreign Application Priority Data

Nov. 29, 1977 [DE] Fed. Rep. of Germany ....... 2753152

[51] Int. Cl.² .......................................... C07D 221/14
[52] U.S. Cl. ........................................ 546/98; 546/99; 252/301; 252/261
[58] Field of Search ................... 260/281; 546/98, 99; 252/301.2 W, 301.3 W

[56] References Cited

U.S. PATENT DOCUMENTS

| | | | |
|---|---|---|---|
| 3,310,564 | 3/1967 | Kasai | 546/98 |
| 3,940,398 | 2/1976 | Wade et al. | 546/98 |
| 3,947,452 | 3/1976 | Wade et al. | 546/98 |
| 3,996,363 | 12/1976 | Wade et al. | 546/98 |
| 4,051,246 | 9/1977 | Wade et al. | 546/98 |
| 4,075,211 | 2/1978 | Scheuermann et al. | 546/101 |
| 4,081,446 | 3/1978 | Papenfuhs | 546/98 |
| 4,151,358 | 4/1979 | Arnold et al. | 546/98 |
| 4,170,651 | 10/1979 | Wade et al. | 546/98 |

FOREIGN PATENT DOCUMENTS 2520642 11/1976 Fed. Rep. of Germany .
2276300 1/1976 France .

OTHER PUBLICATIONS

Seachi et al., "Chem. Abst.", 81:65248d, Sep. 23, 1974.
Ibid, 81:107281s, Nov. 4, 1974.
Hiroshi et al., Ibid, 78:73568m, Mar. 26, 1973.

*Primary Examiner*—Nicholas S. Rizzo
*Assistant Examiner*—David E. Wheeler
*Attorney, Agent, or Firm*—Oblon, Fisher, Spivak, McClelland & Maier

[57] ABSTRACT

Naphthalimide derivatives of the general formula

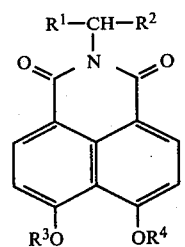

where
$R^1$ is hydrogen or $C_1$- to $C_4$-alkyl,
$R^2$ is nitrile or a radical containing a carbonyl group or an acetalized carbonyl group and
$R^3$ and $R^4$ are unsubstituted or substituted alkyl.

The compounds are excellent optical brighteners, especially for synthetic fibers.

3 Claims, No Drawings

NAPHTHALIMIDE DERIVATIVES

The present invention relates to a compound of the general formula I

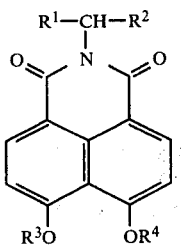

where
$R^1$ is hydrogen or $C_1$- to $C_4$-alkyl,
$R^2$ is a radical of the formula

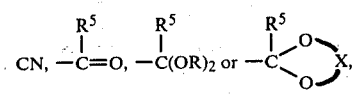

$R^3$ and $R^4$ independently of one another are $C_1$- to $C_4$-alkyl, $\beta$-hydroxyethyl, $\beta$-hydroxypropyl, $\beta$-$C_1$- to $C_4$-alkoxyethyl or $\beta$-$C_1$- to $C_4$-alkoxypropyl,
R is $C_1$- to $C_4$-alkyl,
$R^5$ is hydrogen, $C_1$- to $C_4$-alkyl, hydroxyl, $C_1$- to $C_8$-alkoxy, $\beta$-hydroxyethoxy, $\beta$-$C_1$- to $C_4$-alkoxyethoxy, $\beta$-hydroxypropoxy, $\beta$-$C_1$- to $C_4$-alkoxypropoxy, amino, hydrazino, $C_1$- to $C_4$-alkylamino, or $C_1$- to $C_4$-dialkylamino which are unsubstituted or substituted by hydroxyl or by $C_1$- to $C_4$-alkoxy, pyrrolidino, piperidino, morpholino, piperazino, N-methylpiperazino, $\beta$-dialkylamino- or -trialkylammonium-ethylamino or $\beta$- or $\gamma$-dialkylamino- or -trialkylammonium-propylamino and
X is —$CH_2$—$CH_2$—, —$CH_2CH_2CH_2$—,

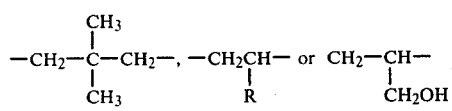

$C_1$- to $C_4$-alkyl radicals R, $R^1$, $R^3$, $R^4$ and $R^5$ are n- or i-propyl, n- or i-butyl and, preferably, methyl or ethyl.
Alkoxyalkyl radicals $R^3$ and $R^4$ are, for example, $C_2H_4OC_2H_5$, $C_2H_4OC_3H_7$, $C_2H_4OC_4H_9$,

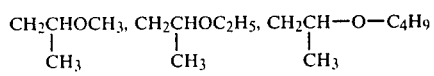

and preferably $C_2H_4OCH_3$.
Specific examples of radicals $R^5$, in addition to those already mentioned, are:

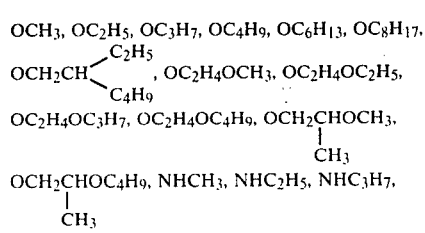

$NHC_4H_9$, $NH(CH_3)_2$, $NH(C_2H_5)_2$, $NH(C_3H_7)_2$, $NH(C_4H_9)_2$, $NHCH_2CH_2OH$, $NHCH_2CH_2CH_2OH$ and $NHCH_2CH_2OCH_3$.

A compound of the formula I may be prepared by reacting a compound of the formula II

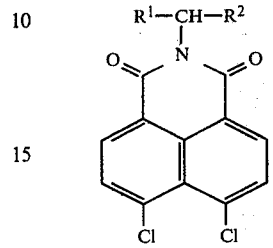

with a compound of the formula

where Me is preferably an alkali metal. The use of mixtures of $R^3OMe$ and $R^4OMe$ is preferred.
Compounds of the formula I, where $R^2$ is $COR^5$, $R^5$ being hydrogen, $C_1$- to $C_4$-alkyl or hydroxyl, are obtained from the corresponding acetals, ketals or esters by hydrolysis.
The reactions are known in principle; details may be found in the Examples, where parts and percentages are by weight, unless stated otherwise.
The compounds of the formula I may be used as optical brighteners for synthetic and cellulosic fibers, especially for polyester and acetate fibers, on which high degrees of whiteness are obtained with small amounts of brightener. The good lightfastness and the greenish white tint also deserve special mention.
Some of the compounds can also be used for mass brightening.
Particularly important compounds are those of the formula Ia

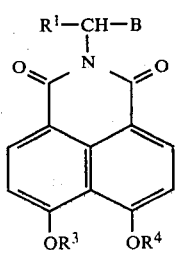

where
B is -CHO,

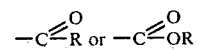

and
R, $R^1$, $R^3$ and $R^4$ have the stated meanings. B is preferably CHO.
Particularly preferred meanings of $R^3$ and $R^4$ are methyl and ethyl. Furthermore, compounds where $R^3$ and $R^4$ are different are preferred.

EXAMPLE 1

87 parts of 4,5-dichloro-N-(1',1'-dimethoxyprop-2'-yl)-naphthalimide, 630 parts of methanol and 78 parts of butyltriglycol are mixed. 146 parts of a 30% strength sodium methylate solution in methanol are added dropwise at 50°-60° C., whilst stirring, and the mixture is then stirred under reflux for 12 hours. When it has cooled, the product is filtered off and washed with 160 parts of methanol and 1,000 parts of water. 80 parts (96% yield) of the compound of the formula

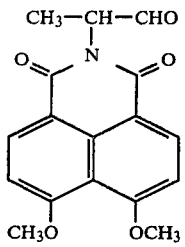

are obtained; after recrystallization from N,N-dimethylformamide, the compound melts at 275°-278° C.

The following compounds were prepared analogously:

| Example | $R^1$ | $R^2$ | $R^3$ | $R^4$ | Melting point (°C.) | Yield (%) |
|---|---|---|---|---|---|---|
| 9  | $CH_3-$ | $-CHO$ | $-C_2H_5$ | $-C_2H_5$ | 261-63 | 91 |
| 10 | $CH_3-$ | $-CHO$ | $-C_4H_9$ | $-C_4H_9$ | 165-67 | 92 |
| 11 | $CH_3-$ | $-CHO$ | $-C_2H_4OH$ | $-C_2H_4OH$ | 242-45 | 98 |
| 12 | $CH_3-$ | $-CHO$ | $-C_2H_4OC_2H_5$ | $-C_2H_4OC_2H_5$ | 188-90 | 192 |
| 13 | $CH_3$ | $-CHO$ | 70% $CH_3-$ 30% $C_2H_5-$ | 70% $CH_3-$ 30% $C_2H_3-$ | 233-35 | 100 |
| 14 | $C_2H_5-$ | $-CHO$ | $-CH_3$ | $-CH_3$ | 262-64 | 90 |

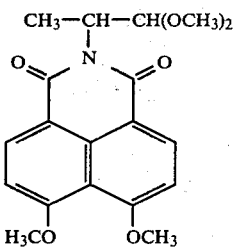

of melting point 178°-179° C. are obtained.

4,5-Dichloro-N-(1',1'-dimethoxyprop-2'-yl)-naphthalimide may be obtained by reacting 4,5-dichloronaphthalic anhydride with 2-amino-propanal-dimethylacetal.

The following compounds were prepared analogously:

| Example | $R^1$ | $R^2$ | $R^3$ | $R^4$ | Melting point (°C.) | Yield (%) |
|---|---|---|---|---|---|---|
| 2 | $CH_3-$ | $-CH(OCH_3)_2$ | $-C_2H_5$ | $-C_2H_5$ | 182-86 | 99 |
| 3 | $CH_3-$ | $-CH(OCH_3)_2$ | $-C_4H_9$ | $-C_4H_9$ | 154-58 | 97 |
| 4 | $CH_3-$ | $-CH(OCH_3)_2$ | $-C_2H_4OH$ | $-C_2H_4OH$ | 179-83 | 69 |
| 5 | $CH_3-$ | $-CH(OCH_3)_2$ | $-C_2H_4OC_2H_5$ | $-C_2H_4OC_2H_5$ | 102-06 | 90 |
| 6 | $CH_3-$ | $-CH(OCH_3)_2$ | 70% $-CH_3$ 30% $-C_2H_5$ | 70% $-CH_3$ 30% $-C_2H_5$ | 185-88 | 92 |
| 7 | $-C_2H_5$ | $-CH\begin{array}{c}O-\\ \\ O-\end{array}\hspace{-2pt}\begin{array}{c}CH_3\\ \\ CH_3\end{array}$ | $-CH_3$ | $-CH_3$ | 213-16 | 98 |

EXAMPLE 15

42 parts of 4,5-dichloro-N-(3'-butyl-2',2'-ethanediolketal)-naphthalimide, 316 parts of methanol and 39 parts of butyltriglycol are mixed. 77 parts of a 30% strength sodium methylate solution in methanol are added dropwise whilst stirring under reflux. After stirring for 12 hours, 11 parts of potassium tertiary butylate are added and stirring under reflux is continued for 8 hours. When the mixture has cooled, the product is filtered off and washed with 160 parts of methanol and 1,500 parts of water. 41 parts (100% yield) of the compound of the formula

EXAMPLE 8

100 parts of 4,5dimethoxy-N-(1',1'-dimethoxyprop-2'-yl)-naphthalimide are added to a solution of 680 parts of N,N-dimethylformamide, 30 parts of water and 2 parts of p-toluenesulfonic acid. The reaction mixture is stirred for 8 hours at 120°-130° C. The product is precipitated with 1,000 parts of water, filtered off and dried. 87 parts (100% yield) of the compound of the formula

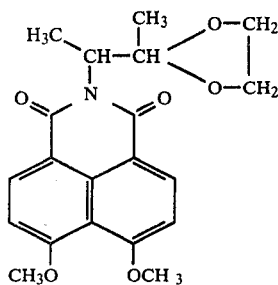

of melting point 192°–194° C. are obtained.

4,5-Dichloro-N-(3'-butyl-2',2'-ethanediolketal)naphthalimide is obtainable by reacting 4,5-dichloronaphthalic anhydride with 3-aminobutanone-2-ethanediolketal.

The following compounds were prepared analogously:

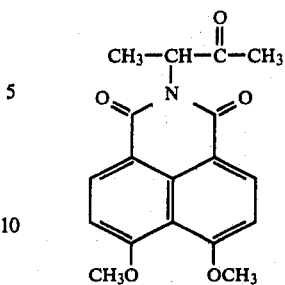

are obtained; after recrystallization from N,N-dimethylformamide, the compound melts at 281°–284° C.

EXAMPLE 24

32 parts of 4,5-dichloro-N-(2'-propionic acid methyl ester)-naphthalimide are introduced into 276 parts of methanol and 34 parts of butyltriglycol. 60 parts of a

| Example | $R^1$ | $R^2$ | $R^3$ | $R^4$ | Melting point (°C.) | Yield (%) |
|---------|-------|-------|-------|-------|---------------------|-----------|
| 16 | CH$_3$— | CH$_3$<br>\|<br>—C(OCH$_3$)$_2$ | CH$_3$— | CH$_3$— | 260–62 | 40 |
| 17 | CH$_3$— | ![structure] | CH$_3$— | CH$_3$— | 198–99 | 67 |
| 18 | CH$_3$— | ![structure] | CH$_3$— | CH$_3$— | 166–68 | 70 |
| 19 | CH$_3$— | ![structure] | CH$_3$— | CH$_3$— | 195–97 | 71 |
| 20 | CH$_3$— | ![structure] | CH$_3$— | CH$_3$— | 215–17 | 56 |
| 21 | CH$_3$— | ![structure] | CH$_3$— | CH$_3$— | 205–06 | 70 |
| 22 | CH$_3$— | ![structure] | CH$_3$— | CH$_3$— | 268–71 | 100 |

EXAMPLE 23

22 parts of 4,5-dimethoxy-N-(3'-butyl-2',2'-ethanediolketal)-naphthalimide are added to a solution of 24 parts of N,N-dimethylformamide and 265 parts of 4 N hydrochloric acid. The reaction mixture is stirred for 40 hours at 100° C. When it has cooled, the product is filtered off and washed acid-free with water. 18 parts (92% yield) of the compound of the formula 30% strength sodium methylate solution in methanol are added dropwise under reflux. Refluxing is continued for 12 hours. After the mixture has cooled, the product is filtered off and washed with 160 parts of methanol and 1,000 parts of water. 31 parts (100% yield) of the compound of the formula

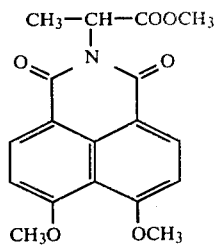

are obtained; after recrystallization from N,N-dimethylformamide, the compound melts at 219°–222° C.

4,5-Dichloro-N-(2'-propionic acid methyl ester)naphthalimide may be obtained by reacting 4,5-dichloronaphthalic anhydride with methyl 2-aminopropionate hydrochloride.

The following was prepared analogously:

| Example | $R^1$ | $R^2$ | $R^3$ | $R^4$ | Melting point (°C.) | Yield (%) |
|---------|-------|-------|-------|-------|---------------------|-----------|
| 25 | H | —COOC$_2$H$_5$ | —C$_2$H$_5$ | —C$_2$H$_5$ | >300 | 100 |

EXAMPLE 26

16 parts of 4,5-dimethoxy-N-(2'-propanaloxime)naphthalimide are added to 264 parts of thionyl chloride. The mixture is stirred for 1.25 hours at 80° C. and, when it has cooled, is stirred into 1,500 parts of ice water. Stirring is continued for 1 hour and the product is filtered off and washed with 2,000 parts of water. 15 parts (97% yield) of the compound of the formula

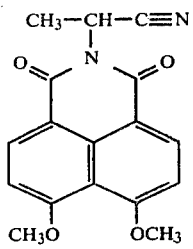

are obtained; after recrystallization from N,N-dimethylformamide, the product melts at >300° C.

4,5-Dimethoxy-N-(2'-propanaloxime)-naphthalimide may be obtained by reacting 4,5-dimethoxy-N-(2'-propanal)naphthalimide with hydroxylamine hydrochloride.

We claim:
1. A naphthalimide having the formula:

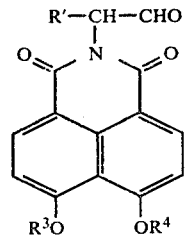

wherein
R' is hydrogen or C$_1$- to C$_4$-alkyl; and,
R$^3$ and R$^4$ independently of one another are C$_1$- to C$_4$-alkyl,
β-hydroxyethyl, β-hydroxypropyl,
β-C$_1$- to C$_4$-alkoxyethyl or
β-C$_1$- to C$_4$-alkoxypropyl.
2. The compound as claimed in claim 1, wherein R$^3$ and R$^4$ are identical or different and are methyl or ethyl.
3. The compound as claimed in claim 2, wherein R$^1$ is methyl.

* * * * *